(12) United States Patent
Schmidt et al.

(10) Patent No.: US 11,486,847 B1
(45) Date of Patent: Nov. 1, 2022

(54) METHOD AND APPARATUS FOR DETERMINING WATER CONTENT OF A FLUID

(71) Applicant: Spartek Systems, Inc., Houston, TX (US)

(72) Inventors: Mathew G. Schmidt, Houston, TX (US); Wai-Ming Tam, Sugar Land, TX (US); Troy M. Thiele, Sylvan Lake (CA); Kenton M. Smith, Red Deer (CA); Guang Cai Meng, Red Deer (CA)

(73) Assignee: SPARTEK SYSTEMS, INC., Houston, TX (US)

( * ) Notice: Subject to any disclaimer, the term of this patent is extended or adjusted under 35 U.S.C. 154(b) by 122 days.

(21) Appl. No.: 16/664,359

(22) Filed: Oct. 25, 2019

(51) Int. Cl.
*G01N 33/28* (2006.01)
*G01N 27/22* (2006.01)

(52) U.S. Cl.
CPC ....... *G01N 27/221* (2013.01); *G01N 33/2823* (2013.01)

(58) Field of Classification Search
CPC .................. G01N 27/221; G01N 33/2823
See application file for complete search history.

(56) References Cited

U.S. PATENT DOCUMENTS

| | | | | |
|---|---|---|---|---|
| 2,907,945 A * | 10/1959 | Bucci | ...................... | H01F 29/06 336/229 |
| 5,562,610 A * | 10/1996 | Brumbach | ...... | A61B 17/320068 604/22 |
| 10,177,696 B1 * | 1/2019 | Holladay | ................... | H02P 8/40 |
| 2012/0215449 A1 * | 8/2012 | Hallundbæk | ............ | G01V 3/26 702/7 |
| 2013/0110411 A1 * | 5/2013 | Black | ...................... | G01N 33/18 702/23 |
| 2014/0043044 A1 * | 2/2014 | Parker | .................... | G01N 27/02 324/633 |
| 2014/0102181 A1 * | 4/2014 | Mohajer | ................ | G01N 27/00 73/61.61 |
| 2019/0118153 A1 * | 4/2019 | Yang | ...................... | B01J 19/087 |
| 2019/0189880 A1 * | 6/2019 | Lin | .......................... | H01L 33/60 |
| 2019/0387604 A1 * | 12/2019 | Fandrich | .............. | H05H 1/2406 |
| 2020/0102232 A1 * | 4/2020 | Holland | .................. | C02F 1/485 |
| 2020/0365315 A1 * | 11/2020 | Kim | ........................ | H01F 17/04 |
| 2020/0393398 A1 * | 12/2020 | Smith | ................ | G01N 33/2847 |

* cited by examiner

*Primary Examiner* — Alvaro E Fortich
*Assistant Examiner* — Zannatul Ferdous
(74) *Attorney, Agent, or Firm* — D'Ambrosio & Menon, PLLC; Usha Menon

(57) ABSTRACT

Methods and apparatus for determining the water cut or the amount of water in fluids. The apparatus is inserted into a production logging tool that is lowered into the well. The apparatus includes a conductive winding which is configured as a first electrode. The winding includes a thin insulation coating or layer. The body of the tool is configured as a ground electrode. The primary electrode and the ground electrode are configured to form a capacitance sensor that generates a signal related to the dielectric permittivity of a fluid flowing between the primary electrode and the ground electrode.

18 Claims, 5 Drawing Sheets

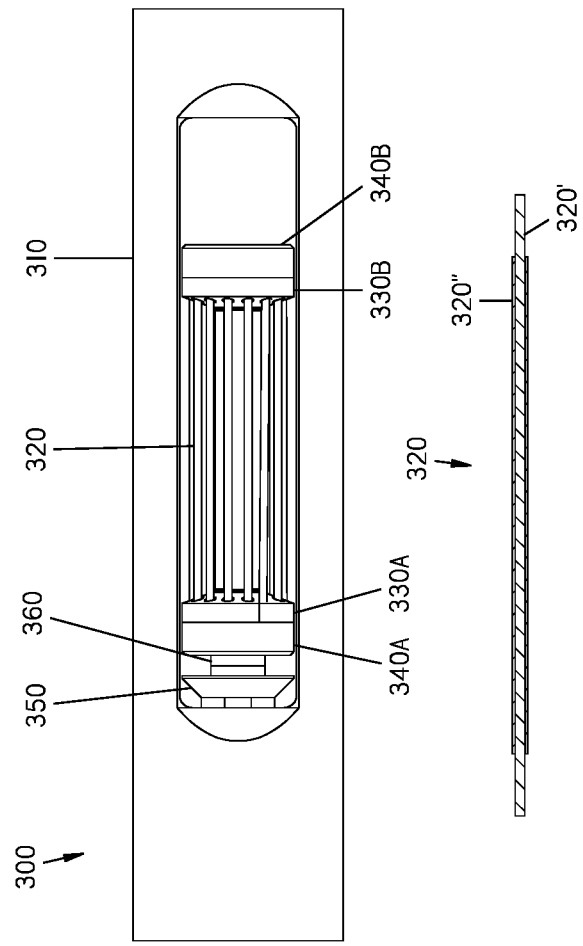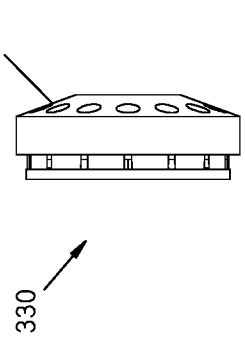

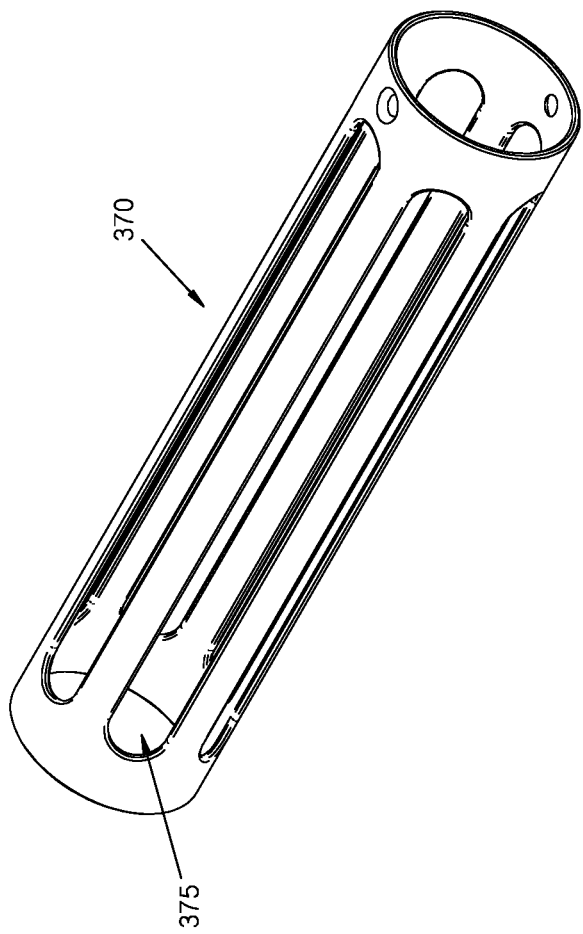

METHOD AND APPARATUS FOR DETERMINING WATER CONTENT OF A FLUID

FIELD OF THE INVENTION

The present invention relates to probes for measuring the water content in a fluid medium.

BACKGROUND

Capacitance is an electrical property of capacitors. It is a measure of the amount of charge that a capacitor can hold at a given voltage. Capacitance (C) is measured in Farad (F) and it can be defined by the unit coulomb per volt:

$$C = \frac{Q}{V} \qquad \text{Equation 1}$$

Where,

C is the capacitance in farad (F),

Q is the magnitude of the charge stored on each plate (coulomb), and

V is the applied voltage to the plates (volts).

When a voltage is applied across the two electrodes of the capacitor, the conducting plates will start to store electrical energy until the potential difference across the capacitor matches with the source voltage. The time required to fully charge a capacitor is determined by the Time Constant ($\tau$). The value of the time constant describes the time it takes to charge a capacitor to 63% of its total capacity. The time constant ($\tau$) is measured in seconds and can be defined as:

$$\tau = RC \qquad \text{Equation 2}$$

The capacitance of a capacitor depends on the geometry of the electrodes (conductors) and not on the external source of charge or potential difference. In general, the capacitance is determined by the dielectric material, distance between the plates or electrodes, and the area of each electrode. For two parallel plates, the capacitance of a capacitor can be expressed in terms of its geometry and dielectric constant as:

$$C = \varepsilon_r \frac{\varepsilon_0 A}{d} \qquad \text{Equation 3}$$

where,

C is the capacitance in farad (F), $\varepsilon$ is the permittivity of the dielectric material, $\varepsilon_r \times \varepsilon_0$ $\varepsilon_r$ is the relative static permittivity (or dielectric constant) of the material between the plates, $\varepsilon_0$ is the permittivity of free space, which is equal to $8.854 \times 10^{-12}$ F/m;

A is the area of each plate, in square meters and d is the separation distance (in meters) of the two plates.

Table 1 shows the relative permittivity or dielectric constant for some common materials.

TABLE 1

| Material | Dielectric Constant |
| --- | --- |
| Air (dry) | 1.000536 |
| Ceramic | 21-38 |
| Petroleum | 2.0-2.2 |
| PEEK (polyetheretherketone) | 3.2 |
| Teflon | 2.1 |
| Water | 80.0 |

The capacitance probe, once it is lowered into a wellbore, can measure the dielectric permittivity of the fluid (water, oil, and/or gas) passing through it. Water has a high dielectric constant which can be distinguished from oil or gas. As water typically coexists with crude oil in petroleum reservoirs, water content, or water cut is an important measure for monitoring wellbore production operations. Water cut measurements are used during production operations in feasibility analyses of oil wells, to determine rates for introducing fluids into a formation or well during recovery methods, in monitoring refining processes, for managing pipeline use, and other such processes.

FIG. 1 represents an exemplary conventional capacitance probe or sensor 100 in a production logging tool. The capacitance probe 100 is generally composed of two electrodes—an insulated primary electrode 110 and a secondary electrode 120. The insulated primary electrode 110 includes a primary electrode 112—comprising a plate or a rod—and insulation material 114 for the primary electrode. The secondary electrode 120 is usually the body of the tool. The insulated primary electrode 110 and the secondary electrode 120 are separated from each other by a dielectric medium (such as, a wellbore fluid) 130. The fluid 125 flows between the insulated primary electrode 110 and the tool body 120.

The capacitance measurement of a production logging tools relies on the change in the permittivity or dielectric constant of the fluid to differentiate between water and hydrocarbons.

Wetting occurs when a film of conductive fluid adheres to the surface of the electrodes which may cause inaccurate measurements of capacitance. For instance, the capacitance probe may sense a higher capacitance than what would be expected based on the fluids surrounding the probe. One source of the wetting is water fallback which causes water to drip on to the capacitance probe creating erroneous readings. Wetting is especially problematic in a wet gas well. In these wells, only a small percentage of the produced fluids is water, sometimes less than 10%, but due to wetting, a false reading of 40% or higher may be observed on the conventional capacitance probes.

As described in FIG. 1, conventional production logging tools utilize an insulated primary electrode in the center of the tool body and uses the metal of the tool body as the second electrode. Wetting of this "center lined" primary electrode can cause problematic/erroneous readings. Similarly, the dynamic range of the probe, that is, the range of acceptable measurement, is also limited by the outer surface area of the electrodes, the thickness of the insulating material, and the dielectric properties of the insulating material.

SUMMARY

According to an embodiment, an apparatus for determining in-situ water content of a fluid, includes a primary electrode having a winding and an insulating material. The insulating material substantially covers the winding. In one or more embodiments, the winding includes a thin insulation layer or coating. The apparatus can be positioned in a body of a production logging tool. The tool body is metallic. The tool body can be configured as a ground electrode. The primary electrode and the ground electrode can be configured to form a capacitance sensor that can generate a signal related to the dielectric permittivity of the fluid.

The fluid comprises a multiphase mixture of water, air and a hydrocarbon. At least a portion of the fluid can flow between the primary electrode and the ground electrode.

The winding can include a pliable, conductive material. In an embodiment, the winding comprises a conductive wire.

The insulating material can be a thermosetting polymer, a thermoplastic polymer or any other suitable non-conductive material.

The apparatus further includes a retaining body. The primary electrode is securely held in position by the retaining body.

In one embodiment, the retaining body comprises a plurality of notches. The primary electrode can be threaded within the plurality of notches in any desired manner.

In another embodiment, the retaining body further comprises at least two retaining members. A first retaining member is spaced apart from a second retaining member at a predetermined distance. A set of complementary radial openings can be formed on a surface of the first and the second retaining members. The primary electrode can be laced between the openings formed on the first and second retaining members. Each retaining member can be provided with a protective end cap. The apparatus can further include a conductive rod. The conductive rod can be coupled to the first and second retaining members and it can function as a secondary electrode. The conductor is at least partially enclosed by the primary electrode. The apparatus can further include a sleeve for the primary electrode. The sleeve comprises a plurality of elongate slots to facilitate fluid flow to the primary electrode.

The retaining body can be coupled to a sub. The sub can provide an electrical connection of the primary electrode to measurement electronics and a signal processing unit.

In another embodiment, a method for determining in-situ water content of a wellbore fluid involves providing an apparatus comprising a primary electrode. The primary electrode has a winding and an insulating material substantially covering the winding. The apparatus can be centrally positioned in a production logging tool. The tool body is configured as a ground electrode. At least a portion of the fluid flows between the primary electrode and the ground electrode. The tool can be run in a completed wellbore. The primary electrode and the ground electrode are configured to form a capacitance sensor to generate a signal related to the dielectric permittivity of the fluid. In general, the more water there in the fluid, the higher its capacitance. The method further involves processing the signal to determine the water content of the fluid.

BRIEF DESCRIPTION OF DRAWINGS

FIG. 3A illustrates a capacitance probe assembly according to another embodiment.
FIG. 3B illustrates a retaining member according to an embodiment.
FIGS. 3C-3D illustrate a sleeve and a sleeved capacitance probe assembly according to an embodiment.

DETAILED DESCRIPTION

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise. Therefore, "for example thermoplastic polymers" means "for example and without limitation thermoplastic polymers" including other plastics and insulators, suitable for use in the oil and gas wells.

The terms "involving", "comprising" and "including" (and similarly "involves", "comprises" and "includes") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error and/or measurement error or limitations.

The terms "primary electrode" and "insulated winding" are used interchangeably.

The one or more embodiments of the present invention relate to an apparatus for determining watercut or in-situ water content of a medium, such as, a surrounding fluid or fluid flowing through a tool. The fluid can include a multiphase mixture of air, water and a hydrocarbon. The hydrocarbon can be in the form of liquid, gas and/or solid in a subsurface environment. In one embodiment, the fluid is a wellbore fluid.

Figure 1:
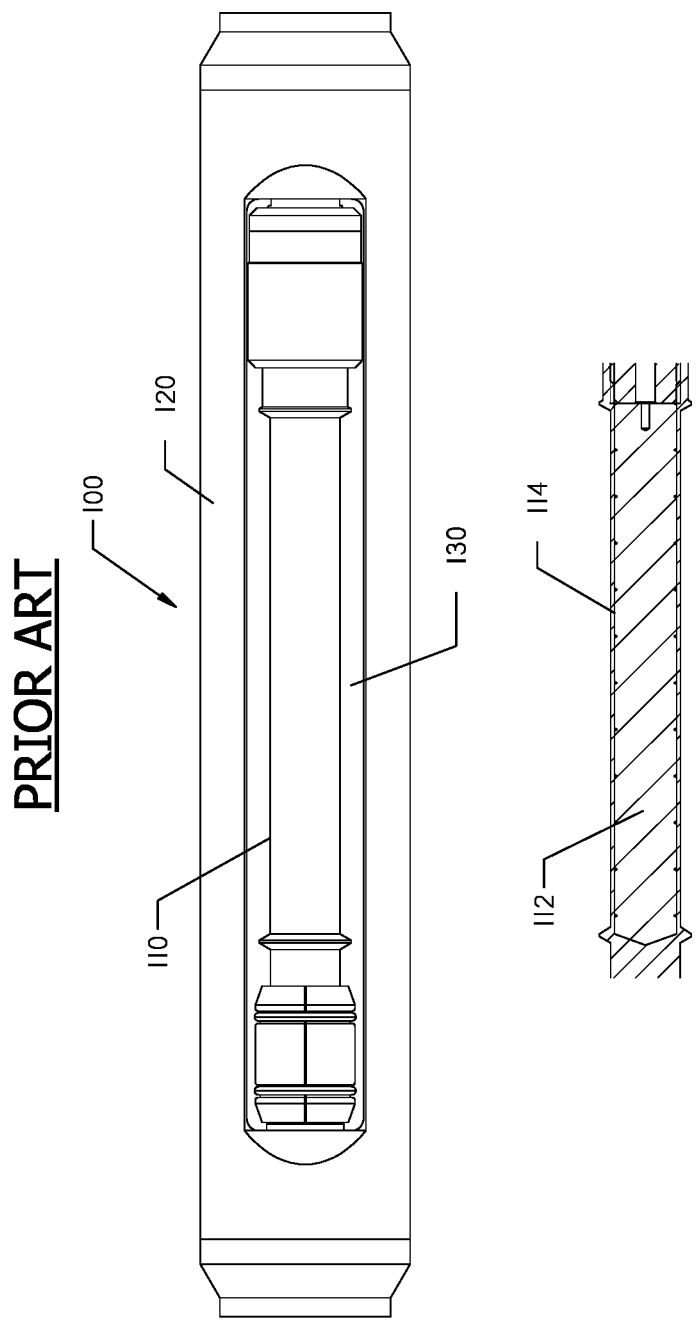
FIG. 1 illustrates a prior art capacitance probe.
Figure 2:
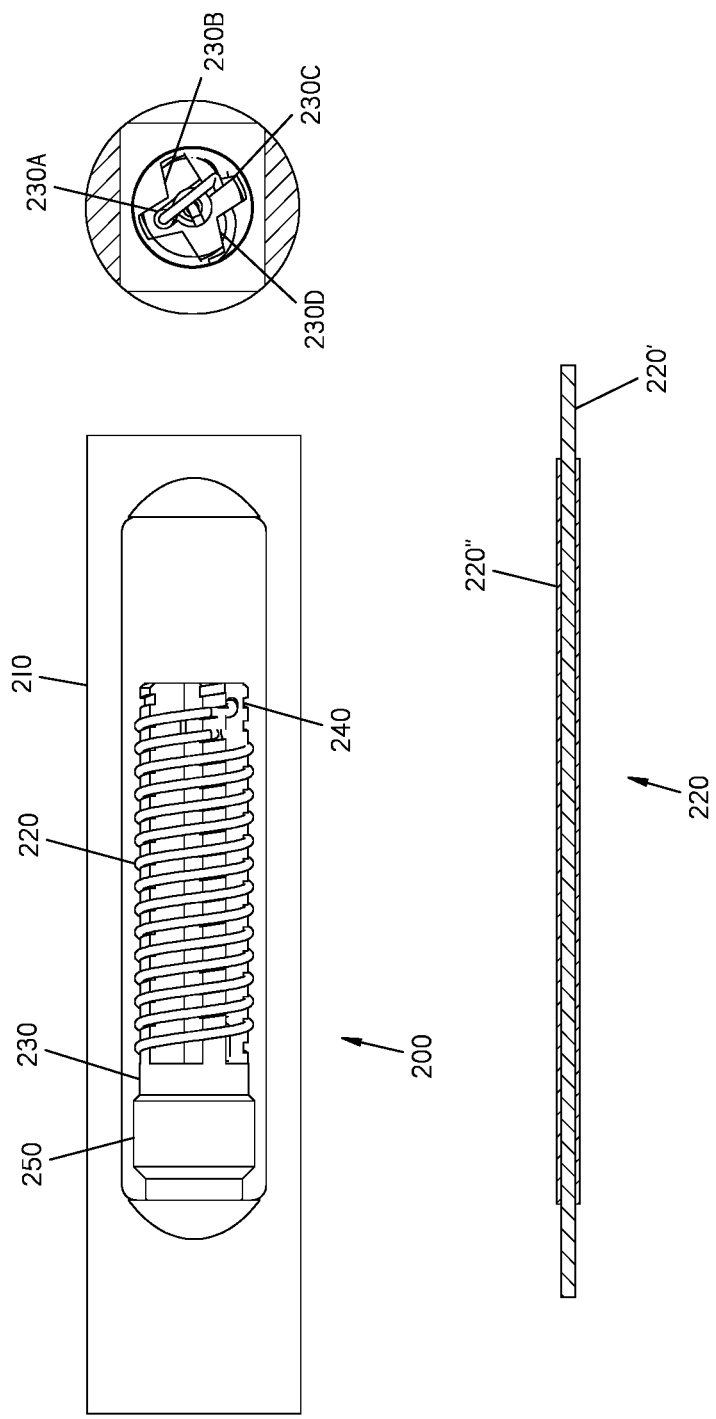
FIG. 2 illustrates a capacitance probe assembly according to an embodiment.

FIG. 2 illustrates an embodiment of the apparatus 200 for measuring water content of a multiphase fluid mixture. The apparatus 200 can be centered in the body of a tool. The tool can include a production logging tool used in an oil and gas well. The body of the tool 210 is metallic and is configured as a ground electrode. In an embodiment, the tool body is cylindrical in shape.

In another embodiment, the apparatus 200 can include a housing (not shown) wherein the housing has any arbitrary shape. For instance, the housing can be elliptical or circular in shape. In another example, the housing can be rectangular in shape. The housing can be configured to function as a ground electrode.

The apparatus 200 includes a primary electrode 220 and a sub 250. The primary electrode 220 is configured as a non-zero voltage electrode. This non-zero voltage primary electrode 220 can be located inside the tool body or inside the housing. The primary electrode 220 may be assigned a different voltage from the ground electrode 210. The arrangement of the apparatus in the tool body functions as a capacitance/capacitive probe that is configured to generate a signal related to the water content of the multiphase fluid mixture. In one or more embodiments, the capacitance probe can be configured to measure the dielectric permittivity of the intervening fluid that surrounds or flows between the ground electrode 210 and the primary electrode 220.

The primary electrode 220 includes a winding element/ winding 220' covered with a layer of an insulation material 220". The winding 220' can include a pliable, conductive material. Without limitation, the winding 220' can include a wire, cable or rod made of a suitable conductive material. In one embodiment, the winding 220' comprises an 18 AWG-24 AWG electrical wire/cable made from copper. The insulation material 220" can include a thermoplastic or a thermosetting polymer. In a specific embodiment, the insulation material is PEEK. However, the insulation material 220" can include any other type of polymer, ceramic or non-conductive material. The radius of the winding 220' is specifically configured to facilitate a reduction in the thickness of the insulation material 220". Advantageously, the winding 220' can be covered with a thin or ultra-thin layer of insulation material 220" which facilitates a substantially accurate measurement of the dielectric permittivity of the intervening fluid. In one embodiment, the insulation material has a thickness of about 0.005 inches-0.015 inches. In one specific embodiment, the insulation material is 0.010 inches in thickness. This increases the dynamic range of the capacitance probe by 200% or greater from traditional probes thereby providing increased sensitivity to small changes in water content.

The primary electrode 220 can be wrapped around a retaining body 230 in any desired manner. In an embodiment, the primary electrode 220 can be wrapped around the retaining body 230 along a lateral plane. The retaining body 230 is coupled to the sub 250. The retaining body 230 can have any desired shape. In one embodiment, the retaining body 230 can have a generally cross-shaped design. The retaining body 230 can be made of a non-conductive material, such as, a thermoplastic polymer or any other suitable insulating material.

The retaining body 230 can be configured with a plurality of notches/grooves 240 along one or more of its surfaces. The notches 240 can have various shapes and depths. The notches may be square, rectangular, circular elliptical or any other convenient shape in cross section. The notches can be positioned in various locations along the retaining body 230. The notches 240 can be sized to have a minimum width less than the width of the insulated winding 220 to frictionally engage it.

As shown in FIG. 2, notches 240 can be formed along a first 230A, second 230B, third 230C and fourth 230D surface of the retaining body 230. The notches are configured to provide a path for the insulated winding 220 as it is wrapped around the retaining body 230. The insulated winding 220 can be looped around each of the notches of the retaining body 230 in one or more pre-determined or arbitrary patterns. In one or more embodiments, the insulated winding can be wound around the retaining body 230 in a circular, helical or spiral pattern or it can be projected as a sinusoidal or square wave.

Sub 250 connects the primary electrode 220 to the tool body. The sub 250 can provide an electrical connection of the primary electrode 220 to measurement electronics and a signal processing unit. Measurement electronics and signal processing units are known in the art and are not shown or described herein. The sub 250 can also serve as a pressure bulkhead. The capacitance can be measured between the centrally located primary electrode 220 and the tool body/housing in which the apparatus 200 is centered.

FIG. 3A illustrates another embodiment of the apparatus for measuring water content of a multiphase fluid mixture. The apparatus 300 includes a primary electrode 320 and a sub 350. The primary electrode 320 is configured as a non-zero voltage electrode. The primary electrode 320 comprises a winding 320' which can be covered with a layer of an insulation material 320".

The winding 320' can include a wire, cable or rod made of a suitable conductive material. In one embodiment, the winding 320' comprises an 18 AWG-24 AWG electrical wire/cable made from copper. The insulation material 320" can include a thermoplastic or a thermosetting polymer. In a specific embodiment, the insulation material is PEEK. However, the insulation material 320" can include any other type of polymer, ceramic or non-conductive material. The radius of the winding 320' is specifically configured to facilitate a reduction in the thickness of the insulation material. Advantageously, the winding 320' can be covered with a thin or ultra-thin layer of insulation material 320" which facilitates a substantially accurate measurement of the dielectric permittivity of the intervening fluid. In an embodiment, the insulation material has a thickness of about 0.005 inches-0.015 inches. In an embodiment, the insulation material is 0.010 inches in thickness.

The primary electrode 320 can be firmly retained in position by a retaining body. In an embodiment, the retaining body includes a pair of complementary retaining members. A first end of the insulated winding or primary electrode 320 can be inserted within a first retaining member 330A and a second end of the insulated winding can be inserted within a complementary second retaining member 330B. The first retaining member 330A and the second retaining member 330B (together "retaining members 330") can be separated by a pre-determined distance and horizontally positioned in a parallel configuration with respect to each other. The retaining members 330 can be made of plastic or any suitable material. The retaining members 330 can have substantially the same size and shape.

As shown in FIG. 3B, the retaining members 330 can be substantially disk-shaped. The retaining members 330 have a set of complementary feed-holes or openings 335 formed substantially adjacent their periphery. Each of the openings 335 is dimensioned to receive the insulated winding 320. The minimum diameter can be less than the outer diameter of the insulated winding 320 to frictionally secure it. The insulated winding 320 can be extended through the pair of retaining members 330.

In an embodiment, a first end of the insulated winding 320 can be initially fitted through a first opening formed on the first retaining member 330A. The second end of the insulated winding 320 can be inserted within a complementary, coinciding first opening formed on the second retaining member 330B. The second end of the insulated winding 320 can be laced through a second opening formed on the second retaining member 330B and then pulled out and inserted into a complementary, coinciding second opening formed on the first retaining member 330A. The process is repeated until the insulated winding 320 is substantially completely threaded in position between the retaining members 330. The insulated winding 320 can form a series of parallel runs along the longitudinal axis which links the opposing retaining members 330A, 330B.

In an embodiment, a suitable restraining means (not shown) may be provided on the free ends of the electrode 320, to prevent egress of opposite ends from the openings 335. In one or more embodiments, the restraining means can include a pair of retaining rings. A first retaining ring can be used to secure a first end of the insulated winding 320 to the first retaining member 330A and a second retaining ring can be used to secure a second end of the insulated winding 320 to the second retaining member 330B.

The first retaining member 330A can be enclosed by a protective end cap 340A and the second retaining member 330B is enclosed by a corresponding protective end cap 340B. The end caps 340A, 340B are insulated. The end caps 340A, 340B ensure that the primary electrode 320 is not damaged by well debris.

A conductor 360 can be centrally coupled to the retaining members 330. The conductor 360 can be a metallic rod. The conductor 360 is configured as a second/secondary electrode. The conductor 360 is at least partially enclosed/ encircled by the primary electrode 320. In one or more embodiments, the conductor 360 comprises a winding element or a conductive wire (not shown). The conductor 360 can also be thinly insulated or isolated electrically (similar to the primary electrode 320). Since the wellbore fluids are conductive, it is important that at least one of the electrodes is electrically isolated from the fluid.

In an embodiment, the apparatus 300 can be centrally placed within the body of a production tool. The tool can include a production logging tool used in an oil and gas well. The tool body 310 is metallic and is configured as a ground electrode. The primary electrode 320 may be assigned a different voltage from the ground electrode 310. The arrangement of the apparatus in the tool body functions as a capacitance/capacitive probe that is configured to generate a signal related to the water content of the multiphase fluid mixture. In one or more embodiments, the capacitance probe can be configured to measure the dielectric permittivity of the intervening fluid that surrounds or flows between the ground electrode 310 and the primary electrode 320. The capacitance can be determined between the primary electrode and the central conductor and the outer tool body. In this configuration, the capacitance sensitivity to fluids is further increased.

Figure 3D:
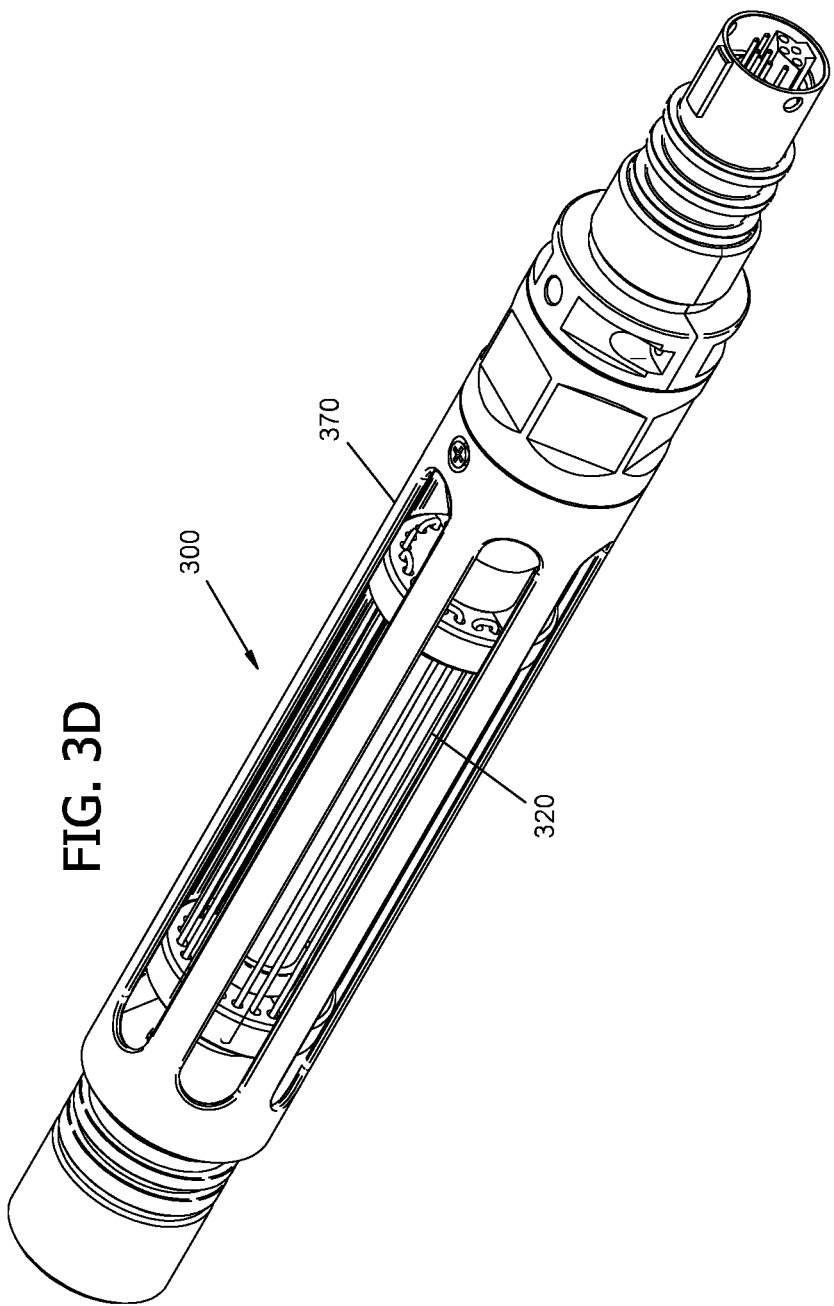

In another embodiment, as shown in FIGS. 3C-3D, the apparatus 300 further includes a protective housing/cover/ sleeve 370 for the primary electrode. The sleeve 370 can be connected to the tool body 310 to hold it in position. For example, the sleeve 370 can be connected to the tool body using screws or other coupling means. The sleeve 370 can be configured with a plurality of elongate slots 375 to allow the passage of fluid to the primary electrode 320.

The primary electrode 320 can be located inside the sleeve 370. The sleeve 370 can also function as a ground electrode. The sleeve 370 can be configured to have any arbitrary shape. In one exemplary embodiment, the sleeve 370 can be circular or elliptical in shape. In another embodiment, the sleeve 370 can be rectangular or square in shape. In yet another embodiment (not shown), the primary electrode 320 can be located external to the sleeve 370.

Sub 350 connects the primary electrode 320 to the tool body via retaining member 330A. The sub 350 can provide an electrical connection of the primary electrode 320 to measurement electronics and a signal processing unit. Measurement electronics and signal processing units are known in the art and are not shown or described herein. The sub 350 can also serve as a pressure bulkhead. The capacitance can be measured between the centrally located primary electrode 320 and the tool body/housing in which the apparatus 300 is centered.

Although only one insulated winding or primary electrode is depicted in the embodiments disclosed herein, it is understood that the apparatus 200, 300 can include more than one insulated winding and any such modifications are within the scope of the invention.

Conventional downhole capacitance probes are susceptible to continuous thin films of conductive fluid, such as, water, due to the large diameter central electrode which causes the probe to wet or read anomalously higher capacitance values. Also, due to the large diameter, the insulation is typically five to ten times thicker than that used by winding element/conductive wire which further reduces the sensitivity of the probe to the dielectric properties of the fluid. In contrast, by using the insulated winding disclosed in the one or more embodiments herein, the length of the electrodes can be increased while maintaining a relatively short profile. It also facilitates the adaptation of the spacing and proximity of the primary electrode to the ground electrode.

The use of an insulated winding as the primary electrode can increase the measurement dynamic range and measurement accuracy by enabling the use of substantially thin insulation material. For example, in one embodiment, the insulation can be less than 50 mils (or 0.05 inches) as opposed to 50-150 mils in conventional capacitance probes. The use of the insulated winding element can also eliminate or substantially reduce the impact of wetting.

In one or more embodiments, a plurality of apparatus 200, 300 can be positioned in the tool body. The number and arrangement of the apparatus may depend on the desired measurement.

In another embodiment, a method for determining the water content of a multiphase wellbore fluid mixture involves providing the apparatus having an insulated winding/primary electrode according to an embodiment disclosed herein. The apparatus can be positioned within a production tool. The tool body is configured as a ground electrode. The primary electrode and the ground electrode are configured to form a capacitance probe to determine the dielectric permittivity of the fluid mixture. Production logging tools can be run in completed wells to ascertain the nature and behavior of fluids in or around the borehole during production or injection. The capacitance probe is placed inside a wellbore using any conventional means. Using any conventional power supply, alternating current can be provided to the electrodes. In general, the more water there in the fluid mixture, the higher its capacitance. The capacitance probe can be sampled multiple times a second using a downhole electronic circuit. The capacitance probe is configured to provide signals proportional to the capacitance of the fluid mixture. The signals can be either transmitted to the surface by a wireline telemetry system or it can be stored downhole in non-volatile memory for later retrieval and processing. The method may further involve pre-determining the dielectric constants of the various components of the fluid. The signals can be processed in a dedicated and conventional processor, and based on the pre-determined dielectric constants, the watercut of the multiphase fluid mixture can be determined.

The one or more embodiments of the apparatus disclosed herein are configured to avoid the problems associated with the design of conventional probes by ensuring that the fluid flow seen by the probe is homogenous and representative of the mixture of fluids (oil, water, gas). The apparatus facilitates an increase in both the accuracy and sensitivity of measurement to small changes in the watercut.

In one or more embodiments, the surface of the insulated winding can further be provided with a non-wetting surface to enhance the accuracy of measurements. Further, the one or more embodiments of the apparatus can include a guard electrode to help steer or force the electrical field in a preferred direction, that is, in the measurement direction.

The apparatus can be used by upstream oil and gas companies. In one embodiment, the apparatus can be used in wet gas wells to improve the accuracy of water content measurements. The water content information can be used by operating companies, including independent, medium and large multi-national companies, and national oil companies.

A number of embodiments have been described. Nevertheless, it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments or "other" embodiments may include all or part of "some", "other" and "further" embodiments within the scope of this invention.

We claim:

1. An apparatus for determining in-situ water content of a fluid, comprising:
    a primary electrode, the primary electrode comprising:
        a winding; and
        an insulating material, the insulating material substantially covering the winding,
    wherein the apparatus is positioned in a body of a production logging tool, and wherein the body of the production logging tool is configured as a ground electrode, and
    wherein the primary electrode and the ground electrode are configured to form a capacitance sensor that generates a signal related to a dielectric permittivity of the fluid, and wherein the fluid flows between the primary electrode and the ground electrode, and wherein the winding creates an equipotential electrical field, or virtual surface, to form one of the capacitance electrodes.

2. The apparatus according to claim 1, wherein the winding comprises a pliable, conductive material.

3. The apparatus according to claim 2, wherein the winding comprises a conductive wire.

4. The apparatus according to claim 1, wherein the insulating material is a thermosetting polymer.

5. The apparatus according to claim 1, wherein the insulating material is a thermoplastic polymer.

6. The apparatus according to claim 1, further comprising a retaining body, wherein the primary electrode is securely held in position by the retaining body.

7. The apparatus according to claim 6, further comprising a sub, wherein the sub is coupled to the retaining body.

8. The apparatus according to claim 6, wherein the retaining body further comprises a plurality of notches, and wherein the primary electrode is threaded within the plurality of notches.

9. The apparatus according to claim 6, wherein the retaining body further comprises at least two retaining members, wherein a first retaining member is spaced apart from a second retaining member at a predetermined distance.

10. The apparatus according to claim 9, wherein a set of complementary radial openings is formed on a surface of the first and the second retaining members, and wherein the primary electrode is laced between the openings formed on the first and second retaining members.

11. The apparatus according to claim 10, wherein the first and second retaining members are each provided with a protective end cap.

12. The apparatus according to claim 11, further comprising a conductive rod, wherein the conductive rod is coupled to the first and second retaining members.

13. The apparatus according to claim 12, wherein the conductor is at least partially enclosed by the primary electrode.

14. The apparatus according to claim 13, further comprising a sleeve for the primary electrode.

15. The apparatus according to claim 14, wherein the sleeve comprises a plurality of elongate slots to facilitate fluid flow to the primary electrode.

16. The apparatus according to claim 1, wherein the fluid comprises a multiphase mixture of water, air and a hydrocarbon.

17. A method for determining in-situ water content of a wellbore fluid, the method comprising:
    providing an apparatus comprising a primary electrode, the primary electrode comprising a winding;
    positioning the apparatus in a production logging tool, wherein a body of the tool is configured as a ground electrode, wherein the primary electrode and the ground electrode are configured to form a capacitance sensor that generates a signal related to a dielectric permittivity of the fluid, and wherein at least a portion of the fluid flows between the primary electrode and the ground electrode;
    running the tool in a completed wellbore; and
    determining a dielectric permittivity of the fluid, wherein the primary electrode and the ground electrode are configured to form a capacitance sensor for generating a signal related to the dielectric permittivity, and wherein the winding creates an equipotential electrical field, or virtual surface, to form one of the capacitance electrodes.

18. The method according to claim 17, further comprising providing a thin insulating coating or layer over the winding.

* * * * *